US006251401B1

(12) United States Patent
Ceccarini et al.

(10) Patent No.: US 6,251,401 B1
(45) Date of Patent: Jun. 26, 2001

(54) COMBINED MENINGITIS VACCINE

(75) Inventors: Costante Ceccarini, Castelnuovo Berardenga; Paolo Costantino; Sandro D'Ascenzi, both of Colle Val D'Elsa; Francesco Norelli; Aldo Giannozzi, both of Siena, all of (IT)

(73) Assignee: Chiron S.p.A., Siena (IT)

( * ) Notice: Subject to any disclaimer, the term of this patent is extended or adjusted under 35 U.S.C. 154(b) by 0 days.

(21) Appl. No.: 08/836,080

(22) PCT Filed: Nov. 2, 1995

(86) PCT No.: PCT/IB95/01006

§ 371 Date: May 1, 1997

§ 102(e) Date: May 1, 1997

(87) PCT Pub. No.: WO96/14086

PCT Pub. Date: May 17, 1996

(30) Foreign Application Priority Data

Nov. 2, 1994 (GB) .................................................. 9422096

(51) Int. Cl.$^7$ ...................... A61K 39/385; A61K 39/116; A61K 39/095; A61K 39/102

(52) U.S. Cl. .................................. 424/197.11; 424/203.1; 424/250.1; 424/256.1; 424/234.1; 424/184.1; 424/831; 424/193.1; 424/194.1

(58) Field of Search .............................. 424/184.1, 234.1, 424/250.1, 256.1, 193.1, 194.1, 197.11, 203.1, 831

(56) References Cited

U.S. PATENT DOCUMENTS 4,459,286 * 7/1984 Hilleman et al. ....................... 424/87
5,679,352 * 10/1997 Chong et al. ...................... 424/256.1

FOREIGN PATENT DOCUMENTS 0 088 303    9/1983 (EP) .
WO 9808874 * 3/1998 (WO) .

OTHER PUBLICATIONS

Corbel. Biologicals 22: 353–360, 1994.*
Vella et al. Pediatrics 85 (4 pt 2) : 668–675, 1990.*
Force et al. The Annals of Pharmacotherapy 26 : 1429–1445, 1992.*
Jacob et al. Eur. J. Immunol 16 : 1057–1062, 1986.*
Peeters et al. Injection and Immunity 60 (5) : 1826–1833, 1992.*
Peeters et al. Injection and Immunity 59 (10) : 3504–3510, 1991.*
Barington et al., "Non–Epitope–Specific Suppression of the Antibody Response to *Haemophilus influenzae* Type b Conjugate Vaccines by Preimmunization with Vaccine Components," *Infect. Immun.*, 1993, 61(2), 432–438.

Barington, T. et al., "Opposite Effects of Actively and Passively Acquired Immunity to the Carrier on Responses of Human Infants to a *Haemophilus influenzae* Type b Conjugate Vaccine," *Infect. Immun.*, 1994, 62(1), 9–14.

Costantino et al., "Development and phase 1 clinical testing of a conjugate vaccine against meningococcus A and C," *Vaccine*, 1992, 10(10), 691–698.

Force et al., "Haemophilus Influenzae Type B Conjugate Vaccines," *Annals Pharmacotherapy*, 1992, 26(11), 1429–1440.

Granoff et al., "Induction of Immunologic Memory in Infants Primed with *Haemophilus influenzae* Type b Conjugate Vaccines," *J. Infect. Dis.*, 1993, 168, 663–671.

Granoff et al., "Antibody Responses to *Haemophilus influenzae* Type b Polysaccharide Vaccine in Relation to Km(1) and G2m(23) Immunoglobulin Allotypes," *J. Infect. Dis.*, 1986, 154(2), 257–264.

Granoff et al., "Differences in the immunogenicity of three *Haemophilus influenzae* type b conjugate vaccines in infants," *J. Pediatr.*, 1992, 121(2), 187–194.

Holmes et al., "Immunogenicity of four *Haemophilus influenzae* type b conjugate vaccines in 17– to 19–month–old children," *J. Pediatr.*, 1991, 118(3), 364–371.

Keeftenberg et al., "An investigation of a mouse model to estimate the potency of the diphtheria component in vaccines," *J. Biol. Stand.*, 1985, 13, 229–234.

Miyamura et al., "Micro cell culture method for determination of diphtheria toxin and antitoxin titres using VERO cells," *J. Biol. Stand.*, 1974, 2, 203–209.

Parke, Jr. et al., "Interim Report of a Controlled Field Trial of Immunization with Capsular Polysaccharides of *Haemophilus Influenzae* Type b and Group C *Neisseria meningitidis* in Mecklenburg County, North Carolina," *J. Infect. Dis.*, 1977, 136, S51–S56.

Schneerson et al., "Preparation, Characterization, and Immunogenicity of *Haemophilus Influenzae* Type b Polysaccharide–Protein Conjugates," *J. Exp. Med.*, 1980, 152, 361–376.

Vella et al., "Immunogenicity of a New *Haemophilus influenzae* Type b Conjugate Vaccine (Meningococcal Protein Conjugate)(PedvaxHIB™)," *Pediatrics*, 1990, 85(4 pt. 2), 668–675.

* cited by examiner

*Primary Examiner*—Lynette R. F. Smith
*Assistant Examiner*—S. Devi
(74) *Attorney, Agent, or Firm*—Doreen Y. Trujillo; Alisa A. Harbin; Robert P. Blackburn

(57) ABSTRACT

A combined vaccine for bacterial meningitis comprises Hib and MenC oligosaccharide conjugates.

7 Claims, 6 Drawing Sheets

A B C D E F

A- STANDARD: B- ACID HYDROLYSATE:
C-, D-, E- OLISACCHARIDES FOR VACCINE PREPARATION:
F- DISCARDED LOW MOLECULAR WEIGHT OLIGOMERS.

COMBINED MENINGITIS VACCINE

The present invention relates to a combined vaccine for the treatment of bacterial meningitis. In particular, the combined vaccine effectively protects against infection by *Haemophilus influenzae* type B (Hib) and *Neisseria meningitidis* (*meningococcus*) serotypes B and C (MenB, MenC).

Bacterial meningitis caused by infection with Hib, MenB and/or MenC represents a worldwide problem. Infection by these organisms can result in permanent disability and death among young children. Recently, however, a conjugate Hib vaccine has become generally available and has resulted in the effective control of Hib infections. Similar vaccines are shortly to become available for MenC infection and also for MenB infection (see Costantino et al., 1992 Vaccine, 10,691–698).

The Hib and meningococcal vaccines are based on conjugates between oligosaccharides derived from the bacterial surface, which define epitopes specific for the bacterium in question, conjugated to carrier proteins, such as non-toxic mutants of diphtheria toxin, for example CRM197.

Combination vaccines are now gaining widespread acceptance in developed countries. The rationale behind the use of combination vaccines, which comprise more than one antigen and are effective to immunise the recipient against a number of diseases, is that the administration cost of the vaccine may be drastically reduced when compared to a larger number of individual vaccines. As the administration cost may exceed the cost of a vaccine by some tenfold, the advantages of combination vaccines are evident where mass vaccination programmes are being considered. Combination vaccines are being actively promoted by the World Health Organisation (see, for example, CVI Forum, No. 5, November 1993, pp. 2–12; CVI Report of the First Meeting of the Consultative Group, Geneva, 16–17 December 1991, pp. 29–32).

These advantages have been recognised for some time, but only three such combination vaccines are currently widely available. The first to be introduced, in the 1950's, was DTP, a killed vaccine against diphtheria, tetanus and pertussis. The formulation of this triple vaccine presented no major problems as the components in the combination are mutually compatible and the preservative (merthiolate) and adjuvant (alum) used in each separate vaccine were identical. Furthermore, it was found that the whole-cell pertussis component enhanced the immune response to the diphtheria and tetanus toxoids.

In the 1960's, a live oral polio vaccine (OPV) was developed containing types 1, 2 and 3 polio viruses. A problem encountered with the formulation of OPV was the presence of interference between the vaccine components, a problem which had not arisen with DTP. The problem has been minimised by optimising the concentration of the various components.

More recently, a third combination vaccine, a live measles, mumps and rubella (MMR) vaccine has been introduced to most developed countries. Again, the concentration of each individual component needs to be adjusted to minimise the interference phenomenon between the components included in this vaccine.

Currently, there is a trend towards the development of supervaccines comprising a larger number of antigens, based on the DTP vaccine.

There are, however, disadvantages in the formulation of supervaccines based on DTP. Recent evidence has shown that administration of the Hib conjugate vaccine together with DTP reduces the effectiveness of the Hib conjugate in comparison with separate administration of DTP and Hib vaccine (see Abstract 300 from 33rd ICAAC2).

Conflicting data exist on the role of immunity of the carrier protein in influencing antibody response to the hapten or oligosaccharide component of a conjugate vaccine. Such influence is critical to the formulation of Hib-MenB/C vaccines, as the carrier proteins used are invariably similar or identical to the antigens included in the DTP vaccine, which is administered to infants at an early age. According to some studies, response to the conjugate is increased by prior exposure to the carrier, while according to others it is suppressed. (Barington, T. et al., Infection and Immunity 62:9–14 (1994); Schneerson, R. et al., J. Exp. Med 152:361–376(1980), Barington T. et al., Infect. Immun.61:432–438 (1993); Peeters, C.C.A.M. et al., Infect. Immun. 59:3504–3510.

It has now been determined that prior exposure to the carrier protein greatly increases response to the Hib conjugate vaccine.

Accordingly, the object of the present invention is to provide a combined Hib and meningococcus vaccine which may be used in the prophylaxis of bacterial meningitis which allows economical, safe and expedient vaccination against the prevalent causes of meningitis.

The invention therefore provides a meningitis vaccine comprising conjugated Hib and MenC oligosaccharides.

The combination vaccine of the invention has been found to 30 be effective in preventing infection by *Haemophilus influenzae* and *Neisseria meningitidis* serotype C, raising antibodies to the administered conjugated capsular oligosaccharides after the first dose. Moreover, the combination vaccine has been shown to be free from interference between the antigens used.

Avantageously, carrier priming may be exploited in order to maximise response to the vaccine. Carrier priming may be carried out by administration of a DTP vaccine.

The MenC component can be formulated in three different preferred configurations: buffered liquid form; lyophilized with a suitable excipient; and ready to use product with pertinent adjuvants. The Hib vaccine is stable after lyophilization with suitable excipient and in a buffered liquid form. In addition the two vaccines, MenC and Hib, can be lyophilized together with a suitable excipient and subsequently resuspended before use with suitable adjuvants. Any combinations of the stable formulations can be mixed prior to use.

The vaccine of the invention may further comprise a conjugate capsular oligosaccharide deriving from *Neisseria meningitidis* serotype B.

The carrier protein to which the oligosaccharide component of the vaccine of the invention is conjugated may be any protein known in the art for such a purpose. For example, it may be tetanus toxoid, diptheria toxoid, an outer membrane protein of *Neisseria meningitidis*, or a mutant or variant thereof.

The oligosaccharides are preferably size-selected and advantageously have a degreee of polymerisation of 4 or more.

The invention further provides a method for the prophylaxis or treatment of meningitis comprising administering to a subject a pharmaceutically effective amount of a combination vaccine according to the invention. The preferred administration regime is to administer at 2, 4 and 6 months of age, intramuscularly.

In a further aspect of the invention there is provided a combination vaccine according to the invention for use in medicine.

Moreover, the invention provides a Hib oligosaccharide conjugate and a *Neisseria meningitidis* serotype C oligosaccharide conjugate for simultaneous separate or sequential administration.

DETAILED DESCRIPTION OF THE INVENTION

Figure 1:
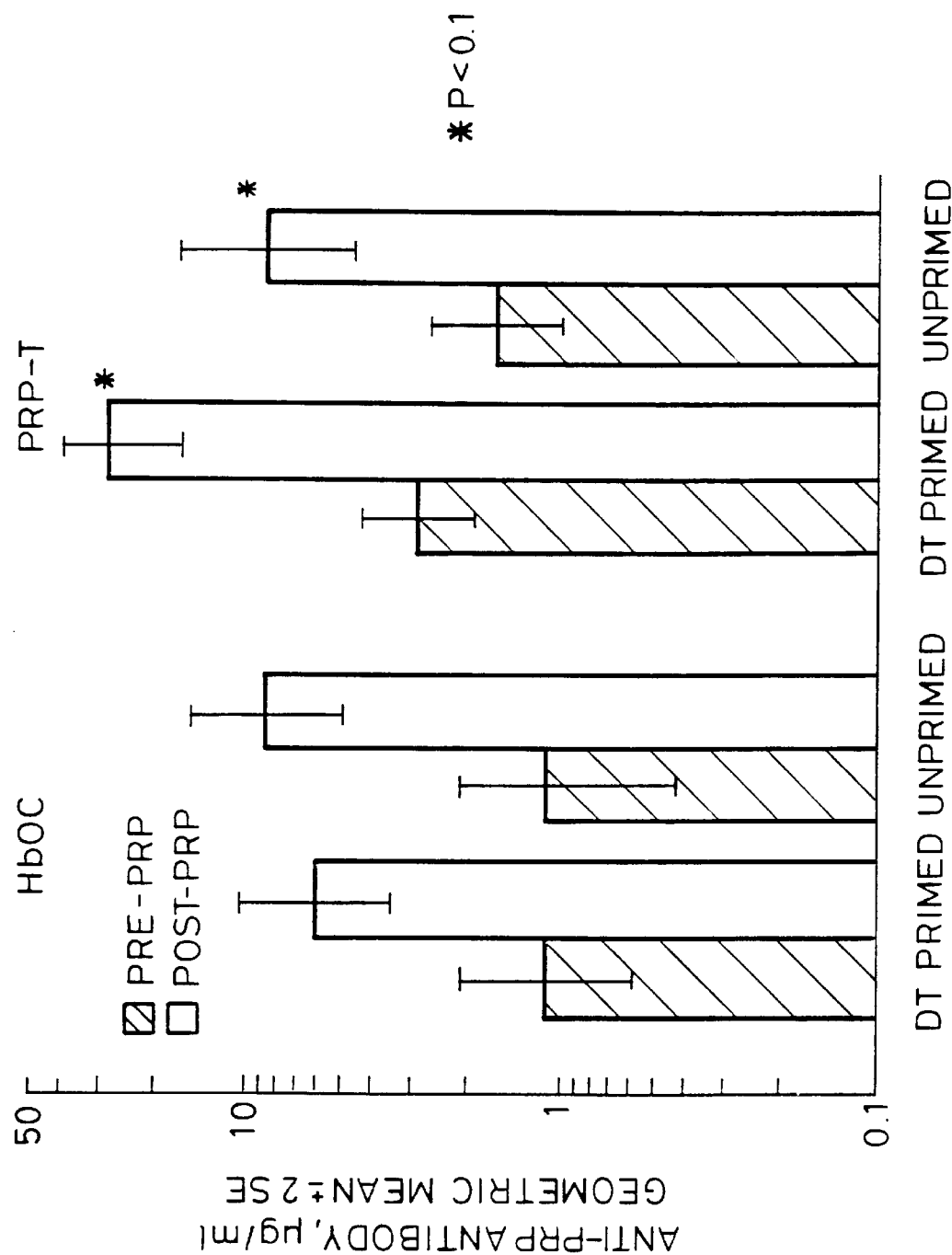
FIG. 1 shows the respective geometric mean antibody concentrations ±2 SE (95% confidence interval) in sera obtained immediately before and 1 month after booster injections in primed and unprimed patients; Antibody Response to PRP Vaccination at 12 Months of Age in Relation to Prior Conjugate Vaccination and DT Priming.

Hib and MenC conjugates may be prepared according to established conjugation technology using oligosaccharides and carrier proteins known in the art. Preferably, however, the conjugates are prepared in accordance with a method which involves sizing of the oligosaccharides in order to exclude short-chain oligomers.

In the case of the Hib vaccine, short chain oligomers have been shown to be poorly immunogenic (Peeters et al., J. Infect. Immun. 60, 1826–1833). Moreover, we have now shown that low molecular weight MenC oligomers are similarly poorly immunogenic. Oligosaccharides having a degree of polymerisation of less than 4 are ineffective in inhibiting the reaction between human antibodies and native polysaccharides in an ELISA test.

The vaccines according to the invention may either be prophylactic (to prevent infection) or therapeutic (to treat disease after infection).

Such vaccines comprise antigen or antigens, usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as further immunostinulating agents ("adjuvants"). Furthermore, the antigen may be conjugated to the bacterial toxoid, such as a toxoid from diphtheria, tetanus, cholera, H. pylori, etc. pathogens.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Immunogenic compositions used as vaccines comprise an immunologically effective amount of the adjuvant and an antigen, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The preferred range is between 2 and 10 µg per dose.

Dosage treatment may be a single dose schedule, although a multiple dose schedule B preferred.

EXAMPLES

Example 1

DETERMINATION OF THE EFFECT OF CARRIER PRIMING WITH Hib CONJUGATE VACCINE

Vaccines and Subjects

The clinical trial was performed at study sites in St. Louis (N=83) and Minneapolis (N=20). 103 healthy infants were randomized at approximately one month of age to either receive a single injection of diphtheria and tetanus toxoid vaccine (DT-primed group), or not to be vaccinated. The DT vaccine (lot 1L21121, Connaught Laboratories, Inc, Swiftwater, PA) was given intramuscularly, using a dose of 0.5 ml. The mean±SD of the ages of the 52 infants given DT was 1.1±0.1. months (Range: 0.8 to 1.3 months). At two months of age, infants in each group were randomized further to receive either three doses of HbOC (lot M695HK), or three doses of PRP-T (lot S2440), administered intramuscularly at 2, 4 and 6 months of age. The dose of HbOC was 10 µg of saccharide and 25 µg of CRM protein in 0.5. ml., and the dose of PRP-T was 10 µg of saccharide and 20 µg of protein, also administered in 0.5 ml. Separate injections of DTP vaccine (0.5 ml, intramuscularly, of lot 2G31010, Connaught Laboratories) were given in the opposite leg at the time of each of the Hib conjugate vaccinations. At 12 months of age, 5 µg of unconjugated PRP vaccine in 0.1 ml was given subcutaneously. The PRP vaccine was provided by NIAID, NIH and has been described previously (Granoff et al., J. INf. Dis. 1993; 168:663–671). Serum samples were obtained immediately prior to each of the Hib conjugate/DTP doses, approximately 4 weeks after the third conjugate dose, and immediately before and 1 month after the PRP vaccination. Ninety-four of the 103 infants (91%) completed the conjugate vaccination protocol and are the subjects included in the analysis reported herein. The nine remaining infants were excluded for the following reasons: difficulty in obtaining blood specimens (1); parents moving out of town (1); no longer wanting to participate (2); lost to follow up (1); inadvertently given the wrong vaccine outside the study (2); diagnosis of underlying immunodeficiency (1); and a febrile seizure unrelated to vaccination (1). The demographic characteristics of the four treatment groups used in the analyses are summarized in Table 1. The groups were similar with respect to gender, race, and age at the first dose of conjugate vaccination.

TABLE 1

Demographic characteristics of the subject groups.

| Vaccine+/<br>DT Priming at 1 mo. | No. of<br>Patients* | %<br>Male | %<br>White | Age (mos)<br>Mean ± SD** |
|---|---|---|---|---|
| HbOC | | | | |
| Primed | 21 | 52 | 90 | 2.0 ± .20 |
| Unprimed | 24 | 33 | 92 | 2.0 ± .16 |
| PRP-T | | | | |
| Primed | 25 | 64 | 96 | 2.1 ± .23 |
| Unprimed | 24 | 63 | 92 | 2.1 ± .22 |

+HbOC (*Haemophilus influenzae* b oligosaccharide-CRM conjugate vaccine); PRP-T (*Haemophilus influenzae* b polysaccharide-tetanus toxoid conjugate); DT (diptheria and tetanus toxoids)
*Data shown are from the 94 infants who completed the conjugate vaccination and were eligible for evaluation (See Methods).
**At time of first dose of conjugate vaccine Adverse Reactions Parents were asked to complete a brief questionnaire noting local reactions at the injection sites, daily temperatures, and other possible systemic reactions occurring during the 72 hours following each dose of DTP/ conjugate vaccination. These observations were supplemented by telephone interviews conducted by the study nurses, and a review of the possible adverse reactions, at the time of each scheduled office visit. Active surveillance for adverse reactions was not performed after the DT vaccination, at 1 month of age; however, information on possible severe reactions to this vaccination was obtained at the 2 month visit, prior to beginning the conjugate/DTP vaccination.

Laboratory

Replicate coded vials of frozen sera were sent to Washington University in St. Louis for measurement in total anti-PRP antibody concentrations, and to Connaught Laboratories, Inc, Swiftater,PA, for measurement of antibody concentrations to diphtheria and tetanus toxoids. All assays were performed without knowledge of DT priming status, or conjugate vaccine assignment.

Total anti-PRP antibody concentrations were measured by a radioantigen binding assay RABA (Granoff et al., J. Inf. Dis. 1986; 154:257–264). The standard curve for the RABA consisted of dilutions of the Hib reference serum pool, obtained from the Center for Biologic Evaluation and Research (CBER), U.S. Food and Drug Administration, Bethesda, MD. The total anti-PRP antibody concentration of this pool was estimated to be 80 $\mu$g/ml. Individual assays included control serum pools representative of a wide range of antibody concentrations (Granoff et al., J. Pediatr. 1992; 121:187–194; Holmes et al., J. Pediatr. 1991; 118:364–371).

Anti-tetanus toxoid and anti-diphtheria toxoid antibody concentrations were measured in serum samples from an approximate 90% sample of the subjects, selected based on completion of the PRP booster protocol prior to April 1993, and the availability of sufficient quantities of serum for the assays.

The anti-tetanus toxoid antibody titers were determined by ELISA. In brief, microtiter plates were incubated overnight at room temperature with purified tetanus toxoid in carbonate buffer, pH 9.6. The plates were washed, and 50 $\mu$l samples of serial two-fold dilutions of test sera and control sera were transferred to the coated plates. After incubation for 3 hours at room temperature, the plates were washed, and bound antibody was detected using alkaline phosphatase-conjugated goat anti-human IgG, IgA and IgM (Kirkegaard and Perry Laboratory, Gaithersburg md.). The concentrations of anti-tetanus toxoid antibody were assigned to the tested sera, in units/ml, by comparison with the antigen binding titration curve of a reference serum pool, prepared at Connaught Laboratory from sera from adults vaccinated with tetanus toxoid. This serum pool was assigned arbitrarily a concentration of 1 unit/ml of antitoxin.

Anti-diphtheria neutralizing antibodies were measured by a micrometabolic inhibition test (Miyamura et al., J. Biol. Stand. 1974; 2:203–209; Keeftenberg et al., J. Biol. Stand. 1985; 13:229–234). In brief, 50 $\mu$l of serial two-fold dilutions of test sera were added to wells of 96 well flat bottom tissue culture plates (Catalogue number 25861, Corning Laboratory Sciences, Corning NY). Diphtheria toxin (25 $\mu$l of a 4-fold excess concentration of the minimal cytopathic dose) was added to all sample wells. VERO cells (African green monkey kidney) were added (25 $\mu$l of 150,000 cells/ml), and a pH indicator was included in the cell culture medium. The cells were incubated at 37° C. for 7 days during which time metabolizing cells show a drop in pH to <7.20, whereas the metabolic activity of diphtheria intoxicated cells is inhibited and a decrease in pH does not occur. Antibody titers were determined by the highest serum dilution giving a pH <7.2 after seven days of incubation. The anti-diphtheria antibody concentrations of the test sera were assigned in units/ml by comparison with the antitoxin activity of dilutions of a known U.S. standard serum (Lot A52, provided by CBER, U.S. Food and Drug Administration, Bethesda, Md.), assayed in parallel with the test samples. Note that a unit of anti-diphtheria toxin antibody and a unit of anti-tetanus toxoid antibody are not equivalent on a weight or activity basis. Therefore, the magnitude of the respective antibody concentrations cannot be compared directly.

Statistical Analysis

Frequency data were compared using Chi square, or Fisher's Exact Test when mandated by small expected frequencies. Antibody concentrations were transformed logarithmically, and the geometric mean antibody concentrations were compared by analysis of variance. For these calculations, antibody concentrations less than the minimum detected in the assay were assigned values of 50% of the minimum (e.g., anti-PRP antibody concentrations <0.07 $\mu$g/ml, anti-tetanus antibody concentrations <0.01 units/ml, and anti-diphtheria antibody concentrations <0.01 units/ml were assigned values of 0.035 $\mu$g/ml, 0.005 units/ml, and 0.005 units/ml, respectively. The antibody responses to conjugate and DT/DTP vaccinations of the infants in Minneapolis and St. Louis were combined since there were no statistically significant differences in the results between the two study sites.

RESULTS

Adverse Reactions

The vaccination regimens were well tolerated. There were no severe reactions, including hypotensive-hyporesponsive reactions, seizures, prolonged screaming episodes, temperatures>39.9° C., in any of the infants. In the four groups, temperature>37.8° was present in 20% to 33% of the infants after DTP/conjugate dose 1, 23% to 29% after dose 2, and 21% to 35% after dose 3. None of the respective differences between vaccine groups was significant (p>0.10)

Immunogenicity

Anti-PRP Antibody Responses to Conjugate Vaccination.

Table 2 summarizes the effect of priming with DT vaccine at 1 month of age on the anti-PRP antibody responses to Hib conjugate vaccine given at 2, 4 and 6 months of age. Prior to the first dose of conjugate vaccine, there were no significant differences in the geometric mean anti-PRP significant differences in the geometric mean anti-PRP antibody concentrations of the four groups. For infants given PRP-T, DT vaccination at 1 month of age increased the geometric mean anti-PRP antibody responses by 2- to 3-fold after each of the three doses of conjugate vaccine compared with the respective geometric means of the antibody responses of the PRP-T vaccinated infants who were not primed with DT. For infants given HbOC, a 2- to 3-fold increase in anti-PRP antibody response also was present in the DT-primed group compared to that of the unprimed group, but only after conjugate dose 1 and 2 (Table 2).

For both conjugate vaccine groups, the proportion of infants who responded to the second dose of the conjugate vaccine with >1 $\mu$g/ml of an anti-PRP antibody was higher for DT-primed infants than unprimed infants (HbOC: 38% vs. 4%, p<0.01; PRP-T: 88% vs. 67%, p=0.10). The corresponding differences were not significantly different after one dose of conjugate vaccine (HbOC: 0% vs. 0%; PRP-T: 20% vs. 4%, p>0.10); or after three doses (HbOC: 86% vs. 88%; PRP=t: 96% vs. 96%, p>0.90).

TABLE 2

Anticapsular antibody responses to Hib conjugate vaccine administered at 2, 4 and 6 months of age in relation to priming with DT vaccine at 1 month.

| Conjugate Vaccine/ DT Priming | No. of Patients | Anti-PRP Antibody Concentration ($\mu$g/ml)* | | | |
|---|---|---|---|---|---|
| | | Before Conjugate Vaccine | After Dose 1 | After Dose 2 | After Dose 3 |
| HbOC | | | | | |
| Primed | 21 | 0.17 (1.75) | 0.16† (1.50) | 0.73# (1.71) | 5.70 (1.82) |
| Unprimed | 24 | 0.15 (1.69) | 0.09† (1.46) | 0.23# (1.65) | 4.50 (1.74) |
| PRP-T | | | | | |
| Primed | 25 | 0.16 (1.64) | 0.37** (1.56) | 4.12** (1.57) | 13.6† (1.51) |
| Unprimed | 24 | 0.19 (1.68) | 0.17** (1.58) | 1.63** (1.58) | 7.9† (1.51) |

+All subjects also received DTP vaccine at 2, 4 and 6 months of age. For vaccine abbreviations, see legend to Table 1.
*Values shown are the geometric means. Values in parentheses are the antilog of 2 S.E. Multiplying and dividing by these values gives the upper and lower bounds, respectively, of the 95% confidence interval of the geometric means.
†.05 < p < .10; comparison of primed vs. respective unprimed group.
**p ≤ .01 after dose 1 and dose 2
p = .003

Memory Antibody Responses to the PRP Booster Vaccination.

Unconjugated PRP was given at 12 months of age to 74 of the 94 infants (79%) who completed the conjugate vaccination. FIG. 1 summarizes the respective geometric mean antibody concentrations±2 SE (95% confidence interval) in sera obtained immediately before and 1 month after the booster injection. Among the PRP-T vaccinated infants, the geometric mean anti-PRP antibody concentration of the DT-primed group was 2.6$\mu$g/ml immediately prior to the PRP booster vs. 1.6$\mu$g/ml in the corresponding infants who did not receive DT (p=0.11). One month after the PRP boost, the geometric mean antibody concentration was 26.4 $\mu$g/ml in the DT-primed group vs. 8.6 $\mu$g/ml in infants who did not receive DT (p=0.01). In the infants given HbOC, there were no significant differences in the respective geometric mean anti-PRP antibody concentrations between DT-primed and unprimed infants before the PRP booster (1.2 vs 1.1 $\mu$g/ml), or 1 month after PRP (6.0 vs. 8.8 $\mu$g/ml, p=0.34).

Anti-diphtheria and Anti-tetanus Antibody Responses.

With one exception, there were no significant differences at two months of age in the respective geometric mean anti-D or anti-T antibody concentrations of the infants vaccinated with DT at 1 month of age and those who were not vaccinated with DT at 1 month of age and those who were not vaccinated with DT (Tables 3 and 4). The exception was that infants randomized to receive PRP-T in the DT-primed group had a 2-fold higher geometric mean anti-T antibody concentration than the corresponding unprimed group (0.06 vs. 0.03 units/ml, p<0.02). This result may have occurred by chance since the opposite trend was observed in the corresponding groups randomized to receive HbOC (0.05 vs. 0.07 units/ml, p>0.10, Table 3).

DT priming at 1 month enhanced the anti-D antibody responses to subsequent injections of DTP and conjugate given at 2, 4 and 6 months. After the first vaccination with DTP/conjugate, the primed infants had 1.5 to 2-fold higher geometric mean anti-d and anti-T antibody concentrations than the respective geometric mean of the unprimed infants (p<0.60); after the second vaccination, the respective geometric means of the primed infants were ~3- to 5-fold higher than those of the unprimed infants (p<0.001). After the third DTP/conjugate vaccination, there appeared to be an interaction between the specific conjugate vaccine used and the respective anti-D or anti-T antibody response. The DT-primed infants vaccinated with PRP-T/DTP had -2-fold higher anti-T antibody concentrations than unprimed infants (p<0.001), but the respective anti-D responses were not significantly different (p>0.20). In contrast, the primed infants vaccinated with HbOC/DTP had ~2-fold higher anti-D antibody concentrations than unprimed infants (p<0.01), but the respective anti-T responses were not significantly different (p>0.24).

TABLE 3

Anti-tetanus toxoid antibody responses to DTP/Hib conjugate vaccination at 2, 4 and 6 months of age in relation to priming with DT vaccine at 1 month.

| Conjugate Vaccine/ DT Priming | No. of Patients | Anti-Tetanus Toxoid Antibody concentration (units/ml) * | | | |
|---|---|---|---|---|---|
| | | Before DTP Vaccine# | After Dose 1 | After Dose 2 | After Dose 3 |
| HbOC | | | | | |
| Primed | 21 | 0.05 (1.49) | 0.05++ (1.43) | 0.15+ (1.32) | 0.29 (1.29) |
| Unprimed | 21 | 0.07 (1.49) | 0.03++ (1.49) | 0.05+ (1.29) | 0.23 (1.28) |
| PRP-T | | | | | |
| Primed | 24 | 0.06** (1.38) | 0.05† (1.29) | 0.15† (1.36) | 0.34† (1.26) |
| Unprimed | 21 | 0.03** (1.43) | 0.03† (1.36) | 0.06† (1.39) | 0.18† (1.28) |

+All subjects also received DTP vaccine at 2, 4 and 6 months of age. For vaccine abbreviations, see legend to Table 1.
*Values shown are the geometric means. Values in parentheses are the antilog of 2 S.E. Multiplying and dividing by these values gives the upper and lower bounds, respectively, of the 95% confidence interval of the geometric means. Data shown are from a 93% sample of subjects (see text).
1 month after DT vaccination in primed groups
++p < .06
†p < .001; comparison of primed vs. respective unprimed group.
**p = .02

TABLE 4

Anti-diptheria toxoid antibody responses to DTP/Hib conjugate vaccination at 2, 4 and 6 months of age in relation to priming with DT vaccine at 1 month.

| Conjugate Vaccine/ DT Priming | No. of Patients | Anti-Diptheria Toxin Antibody Concentration (units/ml)* | | | |
|---|---|---|---|---|---|
| | | Before DTP Vaccine+ | After Dose 1 | After Dose 2 | After Dose 3 |
| HbOC | | | | | |
| Primed | 21 | 0.07 (1.82) | 0.05** (1.65) | 0.23# (1.57) | 0.89† (1.56) |
| Unprimed | 21 | 0.11 (1.82) | 0.02** (1.62) | 0.04# (1.54) | 0.35 (1.54) |
| PRP-T | | | | | |
| Primed | 24 | 0.15 (1.78) | 0.06# (1.44) | 0.19# (1.56) | *0.70† (1.54) |
| Unprimed | 21 | 0.09 (1.91) | 0.03# (1.51) | 0.06# (1.58) | 0.47 (1.58) |

+All subjects also received DTP vaccine at 2, 4 and 6 months of age. For vaccine abbreviations, see legend to Table 1.
*Values shown are the geometric means. Values in parentheses are the antilog of 2 S.E. Multiplying and dividing by these values gives the upper and lower bounds, respectively, of the 95% confidence interval of the geometric means. Data shown are from a 92% sample of subjects (see text).
+1 month after DT vaccination in primed groups
**p = .06
p < .001 comparison of primed vs. respective unprimed group
†<.01; comparison of primed vs. respective unprimed group.

Example 2

SIZE-SELECTION OF IMMUNOGENIC OLIGOMERS

Figure 2:
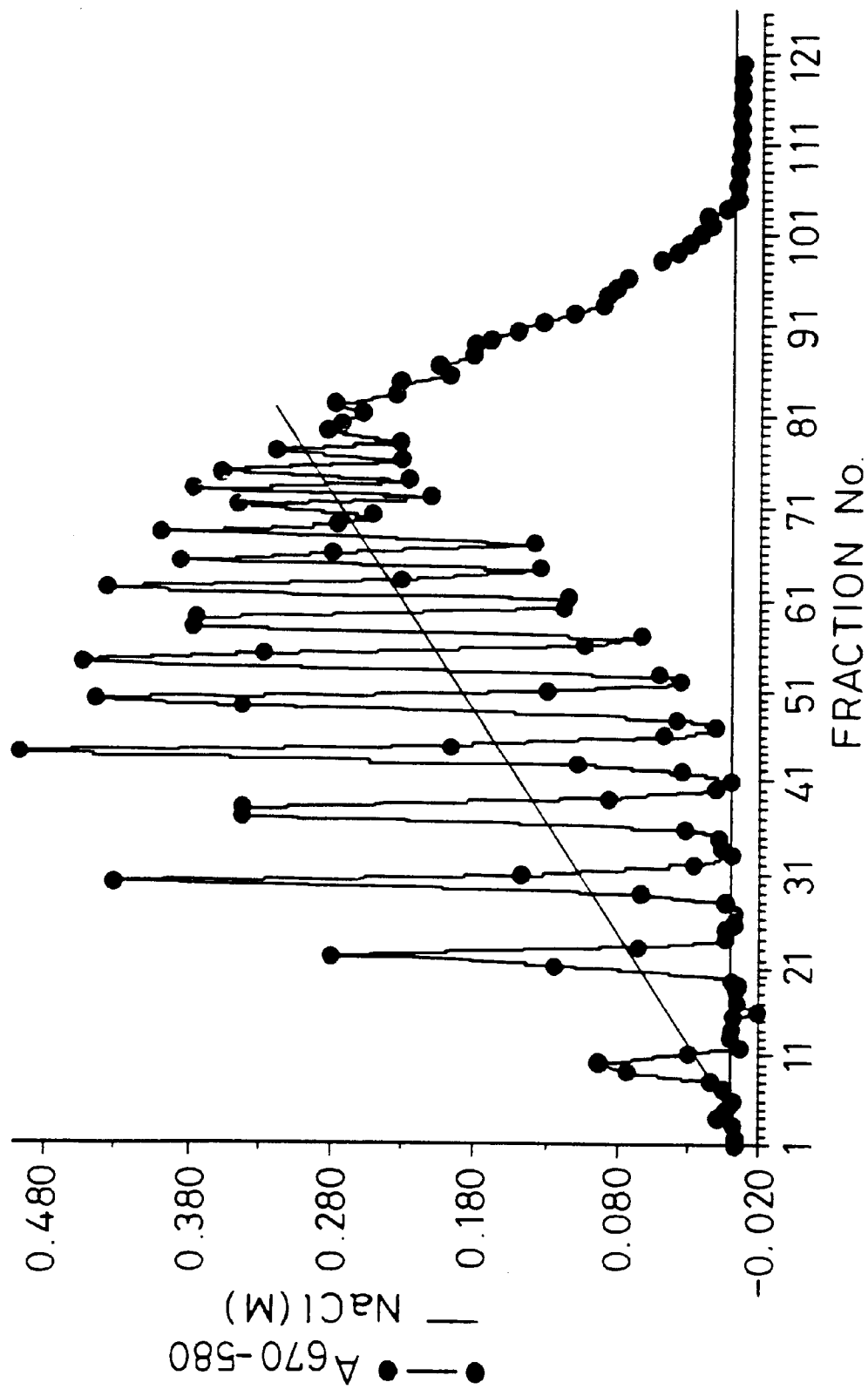
FIG. 2 shows the analytical profile of *H. influenzae* type b oligosaccharides after acid hydrolysis.
Figure 3:
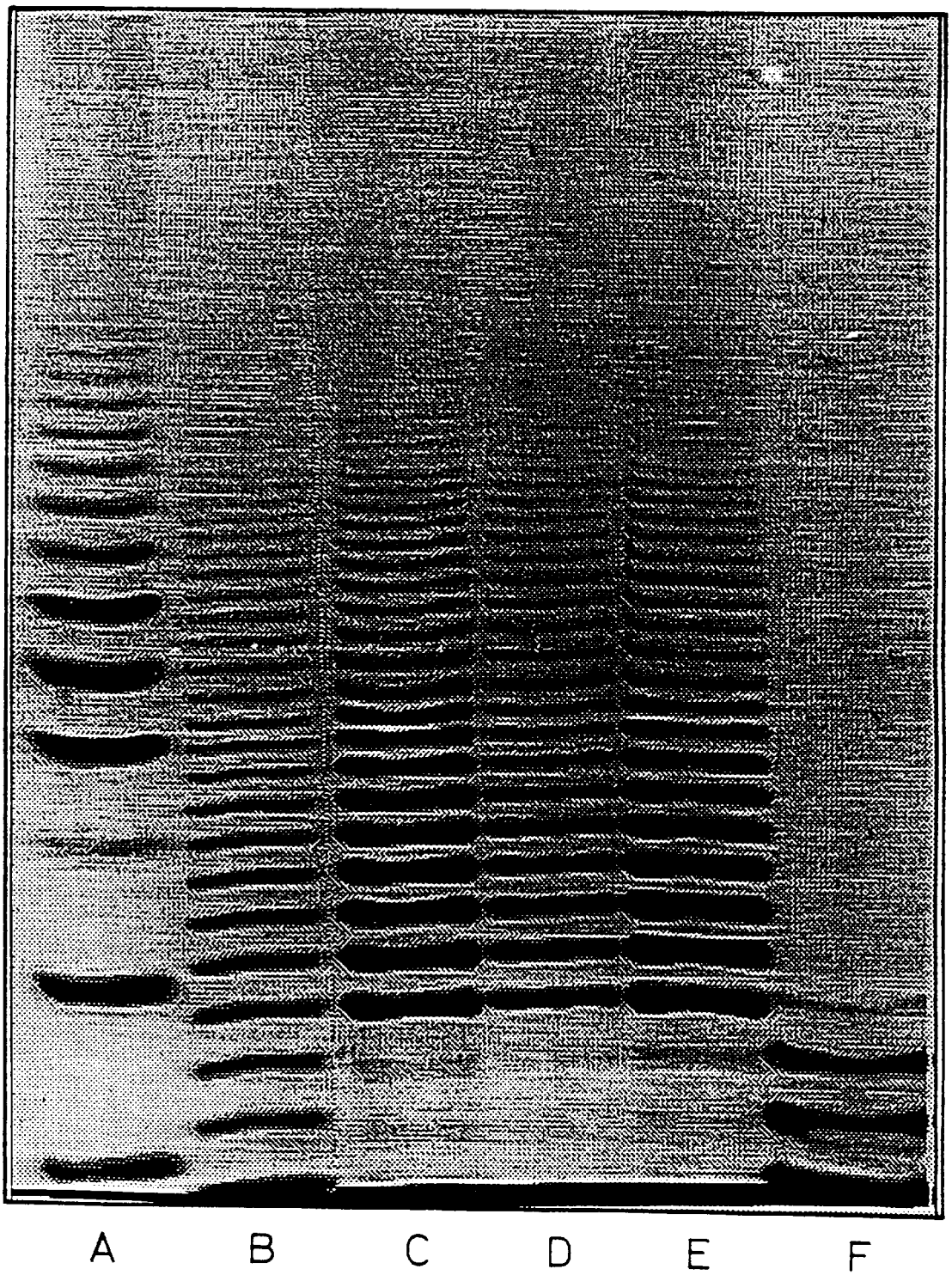
FIG. 3 shows the raw image of a FACE oligosaccharide glycoscan of oligosaccharide preparations before and after size separation.

As an example there is described the selection immunogenic oligomers from *Haemophilus influenzae* type B. After controlled acid hydrolysis at elevated temperature the obtained oligosaccharide preparations comprise oligomers of variable chain length, from single up to relatively longchain oligomers. FIGS. 2 and 3 (lane B) illustrate the heterogeneity of such a hydrolysate. In the illustrated case it is calculated that about half of the oligomer species, on a molar ratio, have a sugar chain of less than 5 sugar residues. When such a hydrolysate is conjugated to a carrier protein, for example CRM-197, they would produce a vaccine product likely to be poorly immunogenic.

Figure 4:
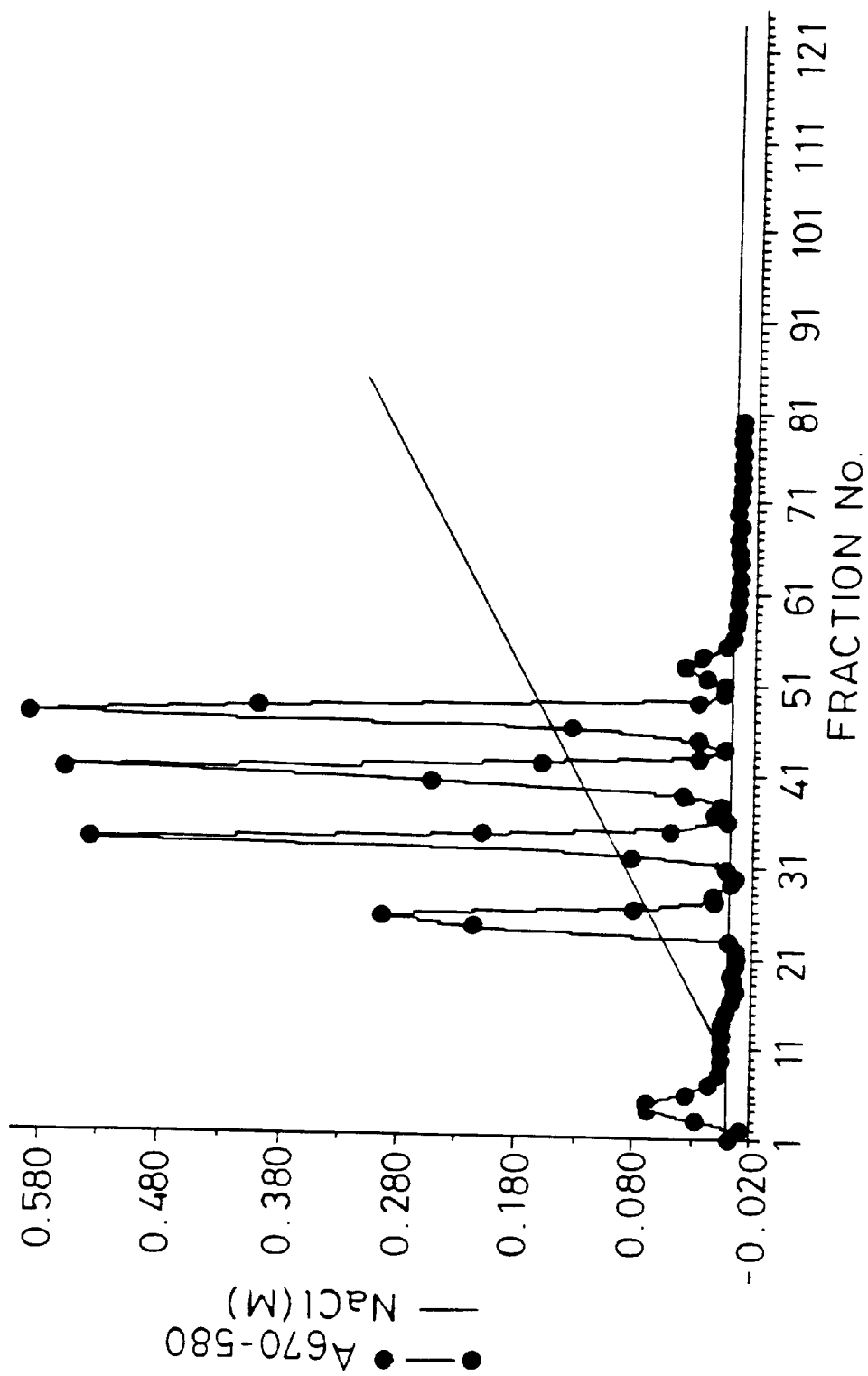
FIG. 4 shows an analytical chromatographic profile of low molecular weight oligomers derived from polysaccharides of *H. influenzae* type b after size separation; the 3 major species are characterised in the mass spectrographic analysis shown in table 4.

To eliminate the un-wanted, short-chain species we have developed a chromatography method that exquisitely permits the separation of the long chain sugar oligomers from the short chain species. The method developed relies on the use of a specific chromatography matrix, Q-Sepharose Fast Flow, and defined salt and hydrogen ion concentrations. The loading salt concentration for eliminating the low molecular weight species can be between 0.05 M and 0.150 M. Preferably, sodium chloride is used. The hydrogen ion concentration should be between $10^{-5}$–$10^{-8}$ M and acetate salts are preferably used. FIGS. 4 and 3 (lane F) show the profile of the low molecular weight species, which are poorly immunogenic.

Figure 5:
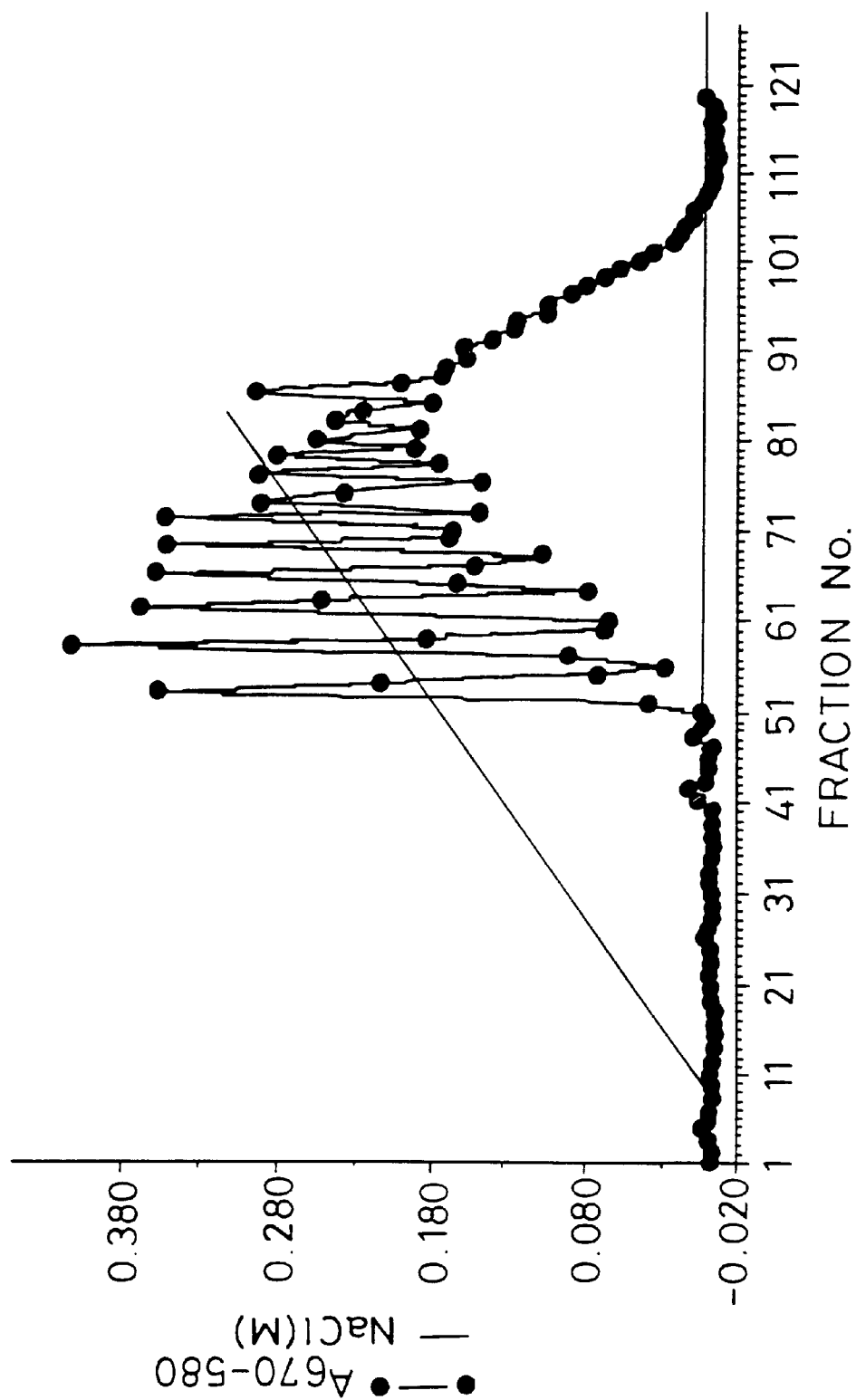
FIG. 5 shows the analytical chromatographic profile of higher molecular weight oligomers derived from the polysaccharides of *H. influenzae* type b, after size separation.

The oligosaccharides to be used for vaccine preparation are eluted with a salt concentration between 0.25 M and 1.0 M, preferably sodium chloride. The chromatographic profile of these higher molecular weight species, used for preparation of the vaccine, is illustrated in FIG. 5. To further reinforce that our chromatographic method can provide a fully defined vaccine product we have analyzed 3 different preparations and these are shown in FIG. 3, lanes C, D and E.

Using mass spectroscopy analyses we have established that our method indeed eliminates the shorter molecular weight species and these have the chain length expected, as shown by the mass spectrographic analysis reported in Table 5. This fractionation method permits the fractionation and specific selection of oligosaccharides from 1 to 60 mg/ml of matrix support.

TABLE 5

Electrospray MS data

| Sample | ESI mw | Theoretical mw | Characterisation. |
|---|---|---|---|
| Peak 3 | 1122 | 1122 (inc Na) | DP3 |
| Peak 4 | 1490 | 1490 (inc Na) | DP4 |
| Peak 5 | 1858 | 1858 (inc Na) | DP5 |

The selected oligosaccharide species can be conjugated to the carrier protein CRM-197 using the chemistry listed below (Costantino et al., Vaccine 10:691–698).

a) Reductive amination of the selected oligosacchrides-introducing a primary amino group at their reducing terminal;

b) Transformation of the amino-oligosaccharides to an active ester by reaction with N-hydroxysuccinimide diester of adipic acid;

c) Coupling of the activated oligosaccharides to CRM-197; and finally the purification of the conjugate for vaccine manufacturing.

Figure 6:
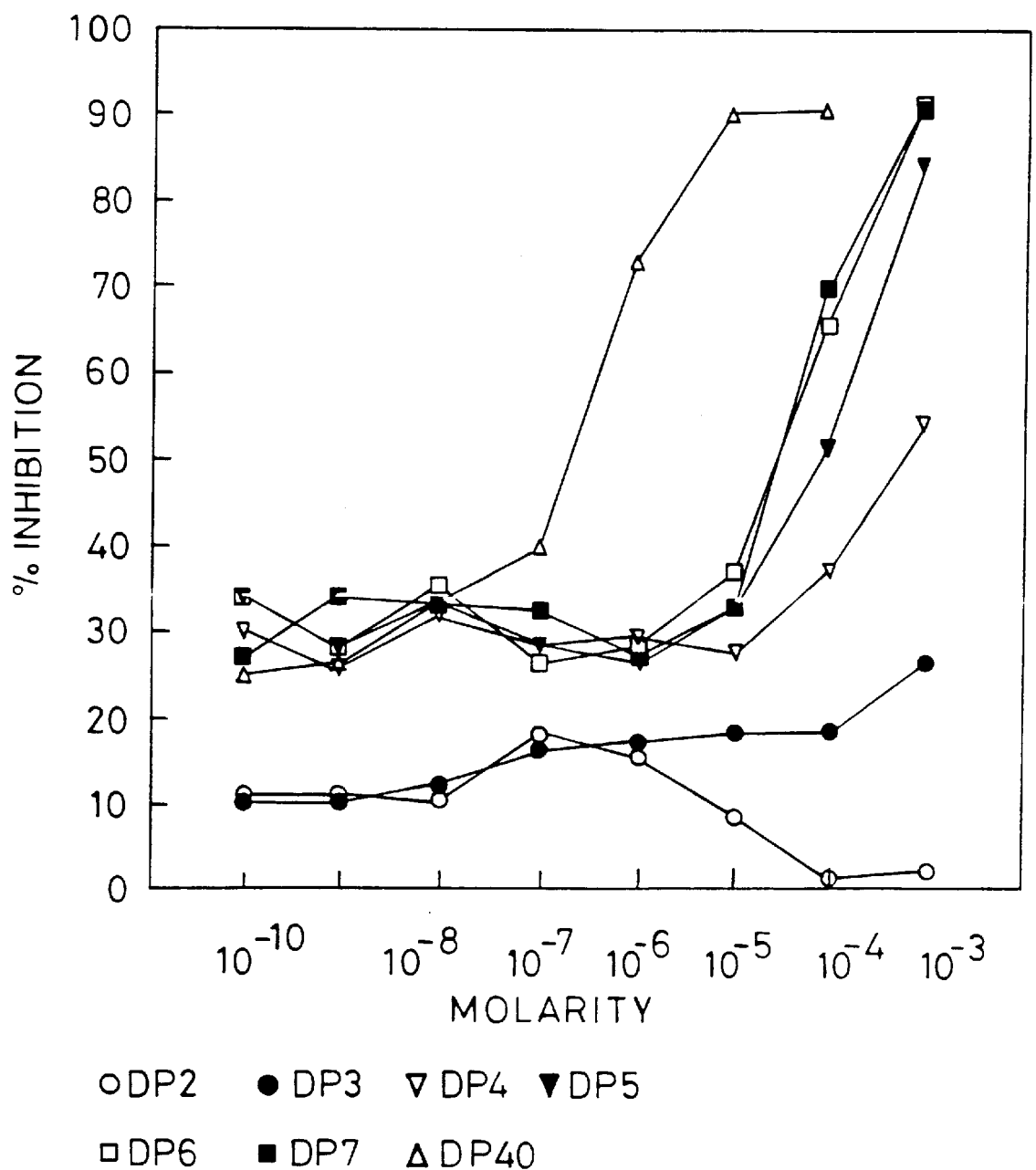
FIG. 6 shows the serum reactivity of MenC oligosaccharides of varying lengths; Competitive Elisa, Pool Human Sera from Adults Vaccinated with Men A+C Polysaccharide Vaccine Inhibited by Men C Oligosaccharides of Different Chain Length.

The method here described has been successfully applied to meningococcus C oligosaccharides and can be clearly applied to all sugar polymers that contain a negative charge moiety, like meningococcus A and B as well as others. FIG. 6 shows the poorly immunogenic nature of Men C oligosaccharides having a degree of polymerisation of less than 4.

What is claimed is:

1. A combination bacterial meningitis vaccine comprising *Haemophilus influenzae* type B and *Neisseria meningitidis* serotype C capsular oligosaccharide conjugates, wherein capsular oligosaccharides of *Haemophilus influenzae* type B and *Neisseria meningitidis* serotype C are size-selected in order to exclude short-chain oligomers having a degree of polymerisation of less than 4.

2. A vaccine according to claim 1 further comprising a *Neisseria meningitidis* serotype B capsular oligosaccharide conjugate.

3. A *Haemophilus influenzae* type B capsular oligosaccharide conjugate and a *Neisseria meningitidis* serotype C capsular oligosaccharide conjugate for simultaneous separate or sequential administration, wherein capsular oligosaccharides of *H. influenzae* type B and *N. meningitidis* serotype C are size-selected in order to exclude short-chain oligomers having a degree of polymerisation of less than 4.

4. A *Haemophilus influenzae* type B capsular oligosaccharide conjugate, a *Neisseria meningitidis* serotype C capsular oligosaccharide conjugate and a *Neisseria meningitidis* serotype B capsular oligosaccharide conjugate for simultaneous, separate or sequential administration, wherein capsular oligosaccharides of *H. influenzae* type B and *N. meningitidis* serotypes C and B are size-selected in order to exclude short-chain oligomers having a degree of polymerisation of less than 4.

5. A method of treating bacterial meningitis comprising administering to a patient a pharmaceutically effective amount of a combination bacterial meningitis vaccine comprising *Haemophilus influenzae* type B and *Neisseria meningitidis* serotype C capsular oligosaccharide conjugates, wherein capsular oligosaccharides of *H. influenzae* type B and *N. meningitidis* serotype C are size-selected in order to exclude short-chain oligomers having a degree of polymerisation of less than 4.

6. A method according to claim 5 wherein the administration of the vaccine is preceded by a carrier priming step.

7. A method according to claim 6 wherein the carrier priming is achieved by administration of a DTP vaccine.

* * * * *